United States Patent [19]

Speranza et al.

[11] Patent Number: 5,391,826
[45] Date of Patent: Feb. 21, 1995

[54] AMIDOPOLYAMINES DERIVED FROM AMINO-CARBOXYLIC ACID

[75] Inventors: George P. Speranza, Austin; Jiang-Jen Lin, Houston, both of Tex.

[73] Assignee: Huntsman Corporation, Salt Lake City, Utah

[21] Appl. No.: 519,079

[22] Filed: May 4, 1990

Related U.S. Application Data

[63] Continuation-in-part of Ser. No. 78,307, Jul. 27, 1987, abandoned.

[51] Int. Cl.⁶ .................. C07C 231/02; C08G 69/10
[52] U.S. Cl. ................................ 564/138; 528/328; 564/141; 564/160
[58] Field of Search .............. 564/138, 141, 160; 528/328

[56] References Cited

U.S. PATENT DOCUMENTS

| | | | |
|---|---|---|---|
| 3,257,342 | 6/1966 | Kwong | 260/18 |
| 3,654,370 | 4/1972 | Yeakey | 260/584 |
| 4,062,819 | 12/1977 | Mains et al. | 260/18 |
| 4,062,820 | 12/1977 | Mitchell et al. | 260/18 |
| 4,119,615 | 10/1978 | Schulze | 528/343 |
| 4,133,803 | 1/1979 | Klein | 528/340 |
| 4,218,351 | 8/1980 | Rasmussen | 260/18 |
| 4,239,635 | 12/1980 | Rieder | 252/34 |
| 4,588,783 | 5/1986 | Chang | 525/329.9 |
| 4,751,255 | 6/1988 | Bentley et al. | 521/163 |

OTHER PUBLICATIONS

Kirk–Othmer, "Encyclopedia of Chemical Technology", John Wiley & Sons, 2nd Edition, vol. 2, pp. 207–208 (1963).

*Primary Examiner*—Peter O'Sullivan
*Attorney, Agent, or Firm*—Russell R. Stolle; Carl G. Ries

[57] ABSTRACT

Diamidopolyamines are prepared by reacting glutamic acid with two moles, per mole of glutamic acid, of a defined class of diamines, including oxyethyelene diamines, oxypropylenediamines, oxyethylene/propylene diamines, oxypropylene triamines, 1,2-diaminocyclohexane and isophorone diamine, whereby each of the carboxyl groups of the glutamic acid will react with an amine group of the amine reactant to thereby provide primary amine terminated amidopolyamines containing, internally, the unreacted primary amine group of the glutamic acid.

14 Claims, No Drawings

AMIDOPOLYAMINES DERIVED FROM AMINO-CARBOXYLIC ACID

RELATED APPLICATION

This application is a continuation-in-part of Lin and Speranza U.S. patent application Ser. No. 07/078,307, filed Jul. 27, 1987, and entitled "AMIDOPOLYAMINES," now abandoned.

BACKGROUND OF THE INVENTION

1. Technical Field of the Invention

This invention relates to diamidopolyamines such as an diamidotriamines. More particularly, this invention relates to novel diamidopolyamines derived from polyoxyalkylene polyamines and glutamic acid. Still more particularly, this invention relates to novel diamidopolyamines prepared by reacting at least about 2 mole equivalents of a polyoxyalkylene diamine or polyoxyalkylene triamine with glutamic acid to thereby couple each of the carboxyl groups of the glutamic acid to an amine group by the formation of an amide linkage therebetween. The reaction is preferably conducted at autogenous pressure at a temperature within the range of about 150° to about 250° C.

The diamidopolyamines of the present invention can be used as raw materials for a wide variety of purposes such as, for example, as chain extenders for epoxy resins, curing agents for epoxy resins, as raw materials for the manufacture of polyureas, thickening agents, etc. The products may also be used as raw materials for the preparation of fuel and lubricant additives, for textile and fiber treating agents, for the preparation of adhesives, for use in the manufacture of polyureas, for use in encapsulation and molding applications, etc.

2. Prior Art

It is known, as exemplified by Yeakey U.S. Pat. No. 3,654,370 to prepare polyoxyalkylene polyamines by the reductive amination of a polyoxyalkylene polyol. The reductive amination is conducted catalytically in the presence of hydrogen and ammonia and an appropriate reductive amination catalyst, such as a nickel, copper and chromia catalyst. The polyoxyalkylene polyamines that are prepared in this fashion are stable articles of commerce having a wide variety of uses such as those mentioned above. In particular, they have found utility as curing agents for epoxy resins, as plasticizers, as cross linking agents and binders for textiles, and as intermediates in the preparation of polyureas. In general, polyoxyalkylene polyamines having molecular weights ranging from about 200 to about 5,000 can be prepared by the Yeakey process.

Kwang. U.S. Pat. No. 3,257,342 is directed to epoxy resins that are cured with a polyamidodiamine prepared by reacting about two molar equivalents of a polyoxyalkylenediamine with an aliphatic dicarboxylic acid.

Klein U.S. Pat. No. 4,133,803 is directed to the preparation of novel thermoplastic adhesive compositions having melting points between 20° and 180° C. prepared by reacting a polyoxypropylene diamine or triamine with an aliphatic or aromatic dicarboxylic acid, ester or anhydride thereof. In his working examples, Klein used approximately equimolar amounts of carboxylic acid and polyamine. However, he states that the molar ratio of the polyoxypropylene diamine or triamine to the dicarboxylic acid may range from about 0.25:1 to about 4.0:1. The thermoplastic adhesives of Klein are made by reacting the polyoxypropylene diamine or triamine with the dicarboxylic acid at about 175° to about 275° C. for about 1 to 12 hours.

The preparation of thermoplastic adhesives is disclosed in Schulze U.S. Pat. No. 4,119,615. The adhesives are prepared by a two-step process. In the first step, about 1 to 4 moles of oxalic acid is reacted with a polyoxyalkylene diamine or triamine, the preferred ratio being a mole ratio of about 1 to 2 moles of oxalic acid per mole of polyoxyalkylene diamine or triamine. This results in the formation of a so-called liquid prepolymer which is then reacted with an alkylene diamine such as ethylene diamine which contain 2 to 18 carbon atoms to provide the resinous polyoxyamide thermoplastic adhesive composition.

Mains et al. U.S. Pat. No. 4,062,819 is directed to polyamide polyblends wherein one component is a high molecular weight thermoplastic polyamide and the other is a minor amount of a polyamide derived from a high molecular weight dibasic acid. The second component is prepared by reacting a dicarboxylic acid such as "dimer acids" with an aliphatic alkylene diamine such as ethylene diamine.

Rieder U.S. Pat. No. 4,239,635 (reissued as U.S. Pat. No. Re.30,885) is directed to lubricants modified by the inclusion of diamides. The diamides are carboxylic acid terminated reaction products of an excess of a dicarboxylic acid with a polyoxyalkylene diamine.

Rasmussen U.S. Pat. No. 4,218,351 discloses impact resistant thermoplastic polyamides which are suitable for use as hot melt adhesives and which contain, as a component, a minor amount of an amorphous amide-forming oligomer which is described as a polyoxyalkylene diamine having a number average molecular weight in the range of about 900 to about 5000.

Mitchell, et al. U.S. Pat. No. 4,062,820 discloses copolyamides derived from a mixture of a polymeric fatty acid and a short chain dibasic acid with a mixture of amines composed of a polyoxyalkylene diamine and a short chain diamine such as ethylenediamine.

Rieder U.S. Pat. No. 4,239,635 is directed to aqueous metal working fluids containing a carboxylic acid group terminated polyoxyalkylene diamine or the alkali metal, ammonium or organic amine salts of the diamides. The diamide is prepared by reacting a dicarboxylic acid with a polyoxyalkylenediamine in a 2:1 mole ratio.

Chang U.S. Pat. No. 4,588,783 relates to heat curable compositions containing polyhydroxyethyl carbonates which are prepared by reacting an amidoamine with an organic carbonate. The amidoamines are prepared by reacting a polyester with an equivalent excess of a polyamine, for example, by reacting two moles of isophorone diamine with one mole of dimethylcyclohexane dicarboxylate.

Bently U.S. Pat. No. 4,751,255 is directed to polymeric polyamines prepared by reacting a polycarboxylic acid or an ester thereof with a stoichiometric excess of a polyamine having terminal aminopropoxy groups to provide polymeric polyamines containing 2 to 4 primary amine groups per molecule.

In Kirk-Othmer, 2nd Edition, Volumne 2, at pages 207-208 it is reported that glutamic acid reversibly dehydrates to pyroglutamic acid, the equilibrium point and rate of reaction varying with pH.

BACKGROUND OF THE PRESENT INVENTION

The polyoxyalkylene polyamines of the type disclosed in Yeakey U.S. Pat. No. 3,654,370 are prepared by the oxyalkylation of a polyhydric alcohol. The preferred starting materials are dihydric and trihydric alcohols such as propylene glycol or glycerol and propylene oxide or ethylene oxide. Copolymer polyols of ethylene oxide and propylene oxide are also useful.

The molecular weight of the polyol is determined by the number of moles of epoxide that are reacted with the alcohol initiator. Since the addition is random, the final alkoxylation product will not be a pure compound but, rather, will be a mixture of polyoxyalkylene polyols. For example, if the polyol is a polyol prepared by reacting glycerol or trimethylol propane with propylene oxide, using an amount of propylene oxide adequate to provide for an average molecular weight of about 1,000, the final propoxylation product will actually be composed of a mixture of polyoxypropylene triols having molecular weights varying from about 800 to about 1,200, the molecular weight distribution following a Gaussian distribution curve (sometimes referred to as a sine curve or a Poissan curve). As the molecular weight of the polyol increases, the spread in the molecular weights will also increase. Thus, when the average molecular weight of the triol is about 3,000, the deviation will be about ±400 molecular weight units so that most of the product will fall within the molecular weight range of about 2,600 to about 3,400.

As the molecular weight is still further increased, the percentage of free hydroxyl groups in the reaction mixture will decrease because of the added bulk of the already formed polyol, thus making the addition of more propylene oxide groups progressively more difficult. As a practical matter, when the triol reaches an average molecular weight of about 5,000, further propoxylation is accomplished only with extreme difficulty. The 5,000 molecular weight polyoxypropylene triols will have a molecular weight distribution of about ±1,000 so that the actual molecular weight range will be from about 4,000 to about 6,000. Again, the molecular weight distribution following a Gaussian distribution curve.

A further complication is encountered during the propoxylation to the higher molecular weights. As the reaction time and temperature are increased to encourage propoxylation, there is introduced a tendency on the part of the propylene oxide to isomerize to allyl alcohol and a tendency on the part of the hydroxypropyl end groups of the polyoxypropylene triol to dehydrate to form a terminal olefin group and water. Both the water and the allyl alcohol are susceptible to oxyalkylation thereby diluting the polyoxypropylene diol with undesired generally low molecular weight diol contaminants derived from the water and monofunctional allyl alcohol propoxylates. From as little as one percent to as much as ten percent of the oxypropyl end groups of the triol may dehydrate to form groups with terminal unsaturation in increasing the average molecular weight from about 3,000 to about 5,000.

When a polyoxypropylene polyol of this nature is reductively aminated in accordance with the procedure of Yeakey U.S. Pat. No. 3,654,370, comparatively higher temperatures and longer reaction times are required as the molecular weight of the polyol increases. This can result in the cleavage of the polyol to form undesired and unwanted alkyl ether by-products and hydrogenation of the unsaturated groups on the polyol to form propyl ethers.

Thus, although the results obtained heretofore with polyoxyalkylene diamines and triamines of the type disclosed by Yeakey have been generally satisfactory, problems such as those mentioned above have detracted from the utility of the products.

SUMMARY OF THE INVENTION

In accordance with the present invention, molecular weight distribution and terminal unsaturation problems such as those mentioned above are significantly reduced through the provision of the diamidopolyamines of the present invention which contains terminal primary amine groups analogous in function and reactivity to the primary amine groups of the polyoxyalkylene polyamines of Yeakey et al. but which are characterized by a significantly narrower molecular weight distribution, by significantly lower by-product contamination and by the presence of a differentially reactive internal primary amine group.

Another significant property of the diamidopolyamines of the present invention, as compared with the corresponding polyoxyalkylenepolyamines, is the desirable increase in the "stiffness" or "hardness" that is obtained without otherwise adversely affecting the other properties of the amidotriamine. For example, when the higher molecular weight polyoxyalkylene polyamines are used to cure epoxy resins, the resultant cured epoxy resin will frequently exhibit undesirable flex and hardness properties and other related characteristics attributable to the "rubbery" nature of the high molecular weight polyoxyalkylene polyamines. Thus, it is frequently necessary to use additives and/or fillers to provide a final cured epoxy resin having the desired physical properties. The aromatic amidotriamines of the present invention are significantly stiffer and can be used successfully with lesser quantities of fillers and/or additives or even without such additives.

Also, the presence of the glutamic acid nucleus contributes to the diamidopolyamine product in two significant respects. The additional internal primary amine of the glutamic acid imparts latent curing properties when the diamidopolyamines are used as curing agents or epoxy resins. Also, the nucleus of the glutamic acid contributes to the formation of diamidopolyamine reaction products that are less viscous, and hence, liquid. For example, the amidoamine reaction products prepared by reacting adipic acid with two mole equivalents per carboxyl group of triethyleneglycol diamine (Jeffamine ® EDR-148) or tetraethylene glycol diamine (Jeffamine ® EDR-192) are solid materials.

The improvements of the present invention are obtained by reacting glutamic acid with two moles, per mole of glutamic acid, of a primary diamine or triamine, as hereinafter defined, to provide an amidoamine condensation product formed by coupling each carboxyl group of the glutamic acid, through an amide group, with a primary amine group of the primary diamine or triamine to provide an amidoamine containing terminal primary amine groups.

Preferred diamine reactants are polyoxyalkylenediamines selected from the group consisting of oxyethylenediamines, oxypropylenediamines, oxypropylenetriamines and oxyethylene/oxypropylenediamines.

When the glutamic acid is reacted with a polyoxyalkylene diamine in accordance with the present invention, the reaction product is a diamidotriamine. When the glutamic acid is reacted with a polyoxypropylene triamine the reaction product is a diamidopentamine. The condensation reaction of the glutamic acid with a polyoxyalkylene diamine or polyoxyalkylene triamine in accordance with the present invention normally results in the provision of a liquid diamidopolyamine reaction product. If the reaction product has excessive viscosity or is solid, the viscosity can be lowered by using a mixture of two or more of the polyoxyalkylene diamines or two or more of the polyoxyalkylene triamines as feed materials.

The reaction between the primary diamine or triamine and the glutamic acid is preferably conducted in an autoclave at a temperature of about 150° to about 250° C. The reaction is preferably conducted at atmospheric pressure. Although there is no particular advantage in doing so, the reaction can be conducted at a higher or lower pressure, such as a pressure ranging from 40 mm of mercury to about 3000 psig.

The reaction time required for completion of the reaction will normally range from about 0.5 to about 12 hours. By-product water of reaction is preferably removed as formed, so that the reaction product obtained at the end of the reaction is the desired final product.

It has been surprisingly discovered that the internal primary amine group of the glutamic acid is essentially unreactive under these reaction conditions.

Thus, it is known that glutamic acid tends to react with itself to form a heterocyclic dicarboxylic dimer in accordance with the equation:

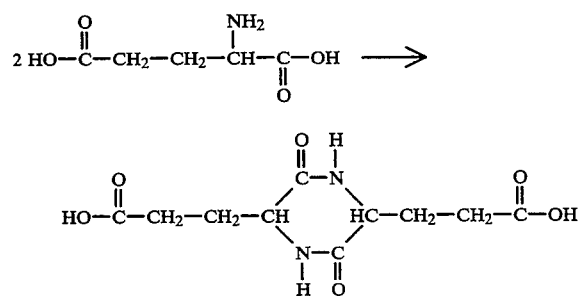

However, this does not present a problem in the practice of the present invention and the reaction product does not contain the dimer even though elevated temperatures are used.

DETAILED DESCRIPTION

The diamidopolyamines of the present invention are obtained by reacting glutamic acid with two moles, per mole of glutamic acid, of a primary diamine or triamine, as hereinafter defined.

The Primary Diamine and Triamine Starting Materials

The primary diamine and triamine starting materials for the present invention are selected from the group consisting of polyoxypropylenediamines, polyoxyethylenediamines, polyoxyethylene/oxypropylenediamines, polyoxypropylene triamines 1,2-diaminocyclohexane and isophorone diamine, as herein defined.

Suitable polyoxypropylene diamines are sold by the Texaco Chemical Company as Jeffamine ® products having the formula:

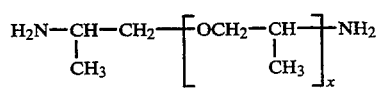

(III)

wherein x is a positive number having an average value of 1 to about 40.

Representative products having this structural formula include polyoxypropylene diols having an average molecular weight of about 230 wherein the value of x is 2.6 (Jeffamine ® D-230 amine), polyoxypropylene diols having an average molecular weight of about 400 wherein x has a value of 5.6 (Jeffamine ® D-400 amine), and a polyoxypropylene diol product having an average molecular weight of about 2,000 wherein x has a value of about 33 (Jeffamine ® D-2000 amine) and a product having an average molecular weight of about 4,000 wherein x has a value of about 60 (Jeffamine ® D-4005 amine).

For example, Jeffamine ® T-403 and Jeffamine ® R-500 will have the formula:

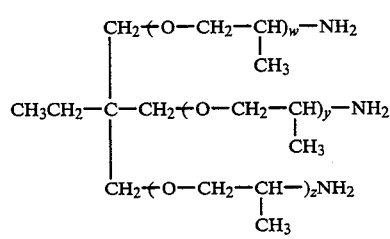

wherein, for Jeffamine ® T-403, the sum of w+y+z will be about 5.3 and for Jeffamine ® T-3000, the sum of w+y+z will be about 50. The addition of propylene oxide is random; the molecules of the prepoxylation product follow a Gaussian distribution pattern. A molecule wherein w and y equal 1 and z equals 98 will not be formed.

It is to be observed that in the above-written formula for Jeffamine ® T-403 and Jeffamine ® T-3000, the 6 carbon atom trivalent hydrocarbon group resulting from the propoxylation of trimethylolpropane will be:

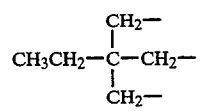

Another appropriate class of polyoxyalkylene diamines, containing both ethylene oxide and propylene oxide, which may be used are polyoxypropylene diamines that are sold by the Texaco Chemical Company as Jeffamine ® ED-series products having the formula:

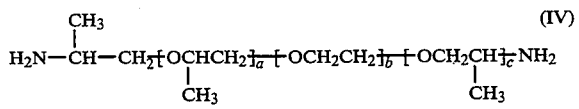

(IV)

wherein a+c equals a number having a value of from about 2 to about 10 and b is a number having a value of from about 1 to about 50.

Examples of products having this general formula include a commercial product having an average molecular weight of about 600 where the value of b is about 13.5 and the value of a+c is about 3.5 (Jeffamine ® ED-600 amine), a commercial product having an average molecular weight of about 900 wherein the value of a+c is again about 3.5, but the value of b is about 20.5 (Jeffamine ® ED-900 amine). Other examples are those wherein a+c has a value of about 3.5 including a product having an average molecular weight of about 2,000 wherein the value of b is about 45.5 (Jeffamine ® ED-2001 amine) and a product having an average molecular weight of about 4,000 wherein the value of b is about 85 (Jeffamine ® ED-4000 amine).

An example of appropriate polyoxypropylene triamines that may be used as a starting material for the present invention include triamines sold by Texaco Chemical Company as Jeffamine ® T-series products having the formula:

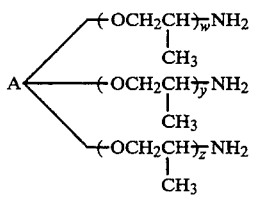

wherein

A represents a trivalent hydrocarbon group consisting of 3 to 6 carbon atoms, resulting from the propoxylation of a propoxylation susceptible trihydric alcohol containing from 3 to 6 carbon atoms, and w, y and z are positive numbers and the average value of the sum of w+y+z is from 4 to about 120.

An example of such a product is a commercial product having an average molecular weight of about 400 wherein A represents a trimethylol propane nucleus (Jeffamine ® T-403 amine) and a product having an average molecular weight of about 5,000 wherein A represents a glycerol nucleus and the product contains about 85 moles of propylene oxide (Jeffamine ® T-5000 amine). The 400 molecular weight product will contain about 5 to about 6 moles of propylene oxide.

It is necessary to express "n" as an average number because, as pointed out above, the addition of ethylene oxide and/or propylene oxide proceeds randomly, and the addition will conform to a Gaussian distribution curve.

For example, if 1 mole of propylene glycol is reacted with 4 moles of ethylene oxide, under ethoxylaton reaction conditions, the reaction, in theory, will proceed as follows:

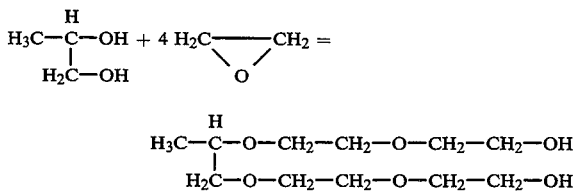

In this situation, R will equal

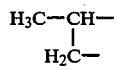

Since the addition of the ethylene oxide proceeds randomly, in conformance with a Gaussian distribution curve, in this example, some of the alkoxylation molecules will contain more than 4 moles of ethylene oxide and some will contain less than 4 moles of ethylene oxide.

The polyol formed by the ethoxylation and/or propoxylation of the divalent or trivalent aliphatic alcohol is reductively aminated, as explained above, to provide the polyoxyethylene/oxypropylene or polyoxypropylene diamine or triamine starting materials of the present invention.

Another group of diamines that may be used are the polyoxyethylenediamines having the formula:

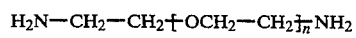

wherein n is a positive integer having a value of 1 to 3.

An example of such a product is bis-aminoethyl ether (BAEE) where n has a value of 1, a product sold by Texaco Chemcial Company under the name Jeffamine ® EDR-148 where n has a value of 2 and a product sold by Texaco Chemcial Company under the name Jeffamine ® EDR-192 where n has a value of 3.

Other diamines that can be used as starting materials include 1,2-diaminocyclohexane and isophorone diamine.

Preparation of the Diamidopolyamines

It has been discovered in accordance with the present invention that a diamidopolyamine condensation product is preferentially formed when glutamic acid is reacted with a primary diamine or triamine of the present invention at a temperature within the range of about 150° to about 250° C. for a reaction time within the range of about 0.5 to about 12 hours. Normally, the reaction will go to completion after a reaction time within the range of about 2 to about 6 hours.

By-product water of the condensation reaction is preferably removed from the reaction mixture as formed. The reaction is complete when essentially all of the carboxylate groups have reacted with primary amine groups of the polyoxyalkylene diamine or triamine. Under the noncatalytic reaction conditions employed herein, the primary amine groups of the polyoxyalkylene diamine or triamine are essentially unreactive with each other and the internal primary amine group is also essentially unreactive.

The diamidopolyamines that are formed by the process of the present invention are liquid or amorphous solid materials having a molecular weight within the range of about 300 to about 15,000 and containing from about 2 to about 6 terminal primary amine groups, depending on the functionality of the starting materials.

EXAMPLE 1 (6199-24): Glutamic Acid and EDR-148 (1:2)

To a 250-ml 3-necked flask equipped with thermometer, stirrer, Dean-Stark trap and N$_2$-inlet line, was charged L-glutamic acid (from Aldrich, 44.1 g, 0.3M)[2] and EDR-148 (triethylene glycol diamine, from Texaco) 88.2 g, 0.6M. No exothermic temperature increase was observed. The mixture was heated to 164°–195° C. The water was collected by means of a Dean-Stark trap. After three hours 9 ml was obtained (theoretical amount 10.8 cc). The reactor was cooled to room temperature. A yellow liquid product (119.5 g) was obtained. The amine analysis showed 7.21 meq/g total amine (calc. 7.37 meq/g) and acidity showed 0.03 meq/g, indicating almost complete reaction. Other analysis including H-nmr proved the product was the two mole adduct of EDR-148 and one mole of glutamic acid.

EXAMPLE 2 (6199-25): Glutamic Acid and EDR-192 (1:2)

A mixture of 44.1 g of glutamic acid and 115 g of EDR-192 (tetraethylene glycol diamine) was heated to 165°–205° C. for 7 hours using the equipment of Example 1. A yellow liquid product (150 g) was recovered. The product was soluble in water and methanol. The analysis indicated 6.00 meq/g for amine (calc. 6.06 meq) and 0.03 meq/g for acidity.

EXAMPLE 3 (6199-25-1): Usage Example

The product of 6199-25 (16.6 g) and Epon 828 (Shell product 37.4 g) were mixed, poured into a mold and cured at 78° C. for overnight. A white, rigid, transparent material was made.

EXAMPLE 4

A series of glutamic acid adducts were prepared using the reaction conditions and reaction procedures of Example 1. The reactants that were used and the results that were obtained are set forth in Table I.

TABLE I

Synthesis of Triamines from Glutamic Acid and Jeffamine ® Amines $$\underset{\text{HOCCH}_2\text{CH}_2\text{CH}-\text{COH}}{\overset{\text{O}\quad\text{NH}_2\quad\text{O}}{\|\quad\;|\quad\;\|}} + \text{JEFFAMINE}^R \text{ AMINE} \longrightarrow$$

$$\underset{\text{H}_2\text{N-JEFFAMINE-NHCCH}_2\text{CH}_2\text{CH}-\text{C}-\text{NH-JEFFAMINE-NH}_2}{\overset{\text{O}\qquad\quad\;\text{NH}_2\quad\;}{\|\qquad\qquad\;|\qquad\;\|}}$$

| Notebook No. | JEFFAMINE Amines | Properties of Products |
|---|---|---|
| 6199-76 | BAEE[1] | Liquid (brown); amine 8.97 meq/g (9.4); acidity 0.05 meq/g |
| 6199-24 | EDR-148 | Liquid (yellow); soluble in H$_2$O, CH$_3$OH; amine 7.21 meq/g (7.3); acidity 0.03 meq/g |
| 6199-25 | EDR-192 | Liquid (yellow); soluble in H$_2$O, MeOH; amine 6.00 meq/g (6.1); acidity 0.03 meq/g |
| 6199-26 | D-230 | Liquid (yellow); soluble in MeOH, insoluble in H$_2$O; amine 4.94 meq/g (5.3); acidity 0.05 meq/g |
| 6199-28 | D-400 | Liquid (yellow); amine 2.74 meq/g (3.2); acidity 0.05 meq/g |
| 6199-81 | D-2000 | Liquid (brown); amine 0.71 meq/g (0.72); acidity 0.03 meq/g |
| 6219-2 | 1,2-diamino-cyclohexane | Solid; amine 6.85 meq/g (calc. 8.8); acidity 0.06 meq/g |
| 6199-88 | IPDA[2] | Solid; amine 6.50 meq/g (calc. 6.6); acid 0.04 meq/g |
| 6219-56 | T-403 | Brown liquid; amine 4.87 meq/g[3] (4.65); acid 0.05 |

(1) Bisaminoethyl ether (NH$_2$CH$_2$CH$_2$OCH$_2$CH$_2$NH$_2$).
(2) Isophorone diamine.
(3) A pentamine was obtained.

The results obtained, as summarized in Table I are surprising because it is known that the primary amine group of glutamic acid is a reactive group, especially at higher temperatures. However, no evidence was obtained indicating the formation of a heterocyclic dicarboxylic acid dimer.

The foregoing examples have been given by way of illustration only and are not intended as limitations on the scope of this invention, which is defined by the appended claims.

We claim:

1. A method of preparing a polyamidopolyamine which comprises reacting glutamic acid with two moles, per mole of glutamic acid, of a primary diamine or triamine, under reaction conditions including a temperature within the range of about 150° to about 250° C., and a reaction time of about 0.5 to about 12 hours to thereby prepare a reaction product composed principally of an amidoamine formed by coupling each carboxyl group of said glutamic acid, through an amide group with a primary amine group of said primary diamine or triamine, whereby an amidoamine condensation reaction product will be provided containing terminal primary amine groups and, internally, the primary amine group of the glutamic acid, said primary diamine or triamine being selected from the group consisting of:

(a) polyoxypropylenediamines having the formula:

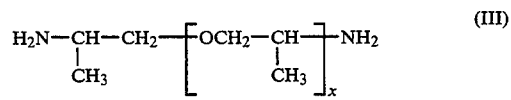

wherein x is a positive number having an average value of 1 to about 40, (b) polyoxyethylenediamines having the formula:

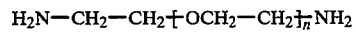

wherein n is a positive integer having a value of 1 to 3, (c) polyoxyethylene/oxypropylenediamines having the formula:

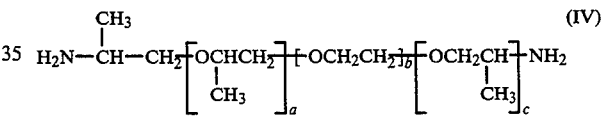

wherein a, b and c are positive integers, wherein a+c equals a positive number having an average value of 2 to about 10 and b is a positive number having an average, value of from 1 to about 50 and, (d) polyoxypropylenetriamines having the formula:

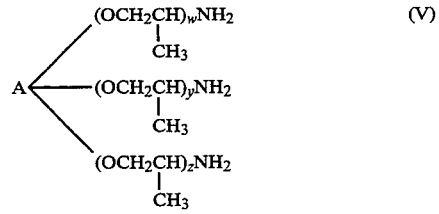

wherein
A represents a trivalent hydrocarbon group consisting of 3 to 6 carbon atoms, resulting from the propoxylation of a propoxylation susceptible trihydric alcohol containing from 3 to 6 carbon atoms,
w, y and z are positive integers and the average value of the sum of w+y+z is a positive number having an average value of from 4 to about 120, (e) 1,2-diaminocyclohexane, and
(f) isophorone diamine.

2. A method as in claim 1 wherein glutamic acid is reacted with an oxypropylene diamine having the formula:

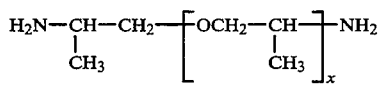 (III)

wherein x is a positive number having an average value of 1 to about 40.

3. A method as in claim 2 wherein x has an average value of 2.6 and the polyoxypropylene diamine has an average molecular weight of about 230.

4. A method as in claim 2 wherein x has an average value of 5.6 and the polyoxypropylene diamine has an average molecular weight of about 400.

5. A method as in claim 2 wherein x has an average value of 33 and the polyoxypropylene diamine has an average molecular weight of about 2,000.

6. A method as in claim 1 wherein glutamic acid is reacted with an oxyethylene diamine having the formula:

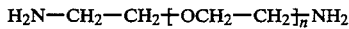

wherein n is a positive integer having a value of 1 to 3.

7. A method as in claim 6 wherein n has a value of 1.

8. A method as in claim 6 wherein n has a value of 2.

9. A method as in claim 6 wherein n has a value of 3.

10. A method as in claim 1 wherein the glutamic acid is reacted with an oxyethylene/oxypropylene diamine having the formula:

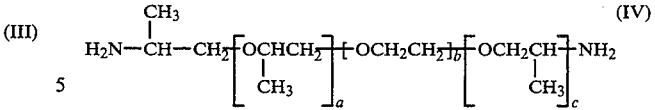 (IV)

wherein a, b and c are positive integers, wherein a+c equals a positive number having an average value of 2 to about 10 and b is a positive number having an average value of from 1 to about 50.

11. A method as in claim 1 wherein the glutamic acid is reacted with an oxypropylene triamine having the formula:

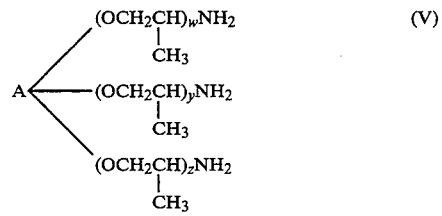 (V)

wherein

A represents a trivalent hydrocarbon group consisting of 3 to 6 carbon atoms, resulting from the propoxylation of a propoxylation susceptible trihydric alcohol containing 3 to 6 carbon atoms, w, y and z are positive numbers and the average value of the sum of w+y+z is from 4 to about 120.

12. A method as in claim 11 wherein A represents a trivalent hydrocarbon group containing 6 carbon atoms resulting from the propoxylation of trimethylolpropane, and the sum of w+y+z is about 5.3.

13. A method as in claim 1 wherein the glutamic acid is reacted with 1,2-diaminocyclohexane.

14. A method as in claim 1 wherein the glutamic acid is reacted with isophorone diamine.

* * * * *